(12) United States Patent
Kim et al.

(10) Patent No.: US 9,610,138 B2
(45) Date of Patent: Apr. 4, 2017

(54) REMOVABLE DENTAL MANDREL GUARD

(71) Applicants: Daniel Sung-Yul Kim, Vancouver, WA (US); Joshua Keelyn Kim, Vancouver, WA (US)

(72) Inventors: Daniel Sung-Yul Kim, Vancouver, WA (US); Joshua Keelyn Kim, Vancouver, WA (US)

( * ) Notice: Subject to any disclaimer, the term of this patent is extended or adjusted under 35 U.S.C. 154(b) by 201 days.

(21) Appl. No.: 14/446,086

(22) Filed: Jul. 29, 2014

(65) Prior Publication Data
US 2015/0037753 A1   Feb. 5, 2015

Related U.S. Application Data

(60) Provisional application No. 61/860,441, filed on Jul. 31, 2013.

(51) Int. Cl.
*A61C 1/16* (2006.01)
*A61C 3/06* (2006.01)
*A61C 1/14* (2006.01)

(52) U.S. Cl.
CPC ............ *A61C 3/06* (2013.01); *A61C 1/145* (2013.01)

(58) Field of Classification Search
CPC .................. A61C 3/06; A61C 1/145
USPC ............. 433/116, 52, 82, 144, 147; 606/79
See application file for complete search history.

(56) References Cited

U.S. PATENT DOCUMENTS

| | | | | |
|---|---|---|---|---|
| 399,350 A | * | 3/1889 | Sisson | A61C 3/06 132/73.6 |
| 1,516,933 A | * | 11/1924 | Terranova | A61C 1/16 29/DIG. 69 |
| 4,693,871 A | * | 9/1987 | Geller | A61C 1/16 433/116 |
| 5,376,003 A | * | 12/1994 | Rizkalla | A61C 17/0202 433/116 |
| 2007/0042319 A1 | * | 2/2007 | Florman | A61C 3/06 433/116 |

* cited by examiner

*Primary Examiner* — Pedro Philogene
*Assistant Examiner* — David C Comstock
(74) *Attorney, Agent, or Firm* — Mark E. Beatty; Rylander & Assoc. PC

(57) ABSTRACT

A removable dental mandrel guard comprising a collar portion extending from a first open end to a transition region, which may include a first tapered portion, the transition region reducing from a first to a second interior diameter; a shaft guard extending from a first end rigidly connected to the transition region to a second end rigidly connected to the disc shield and having interior cross section defining the second interior diameter; a disc shield having opposed first and second transverse walls, each with a partially enclosed perimeter edge joined by coextensive edge wall extending from a first edge point to a second edge point, the interiors of the first and second transverse walls and edge wall defining a disc cavity; a continuous open seam extending longitudinally from the collar portion first open end to the shaft guard second end.

11 Claims, 10 Drawing Sheets

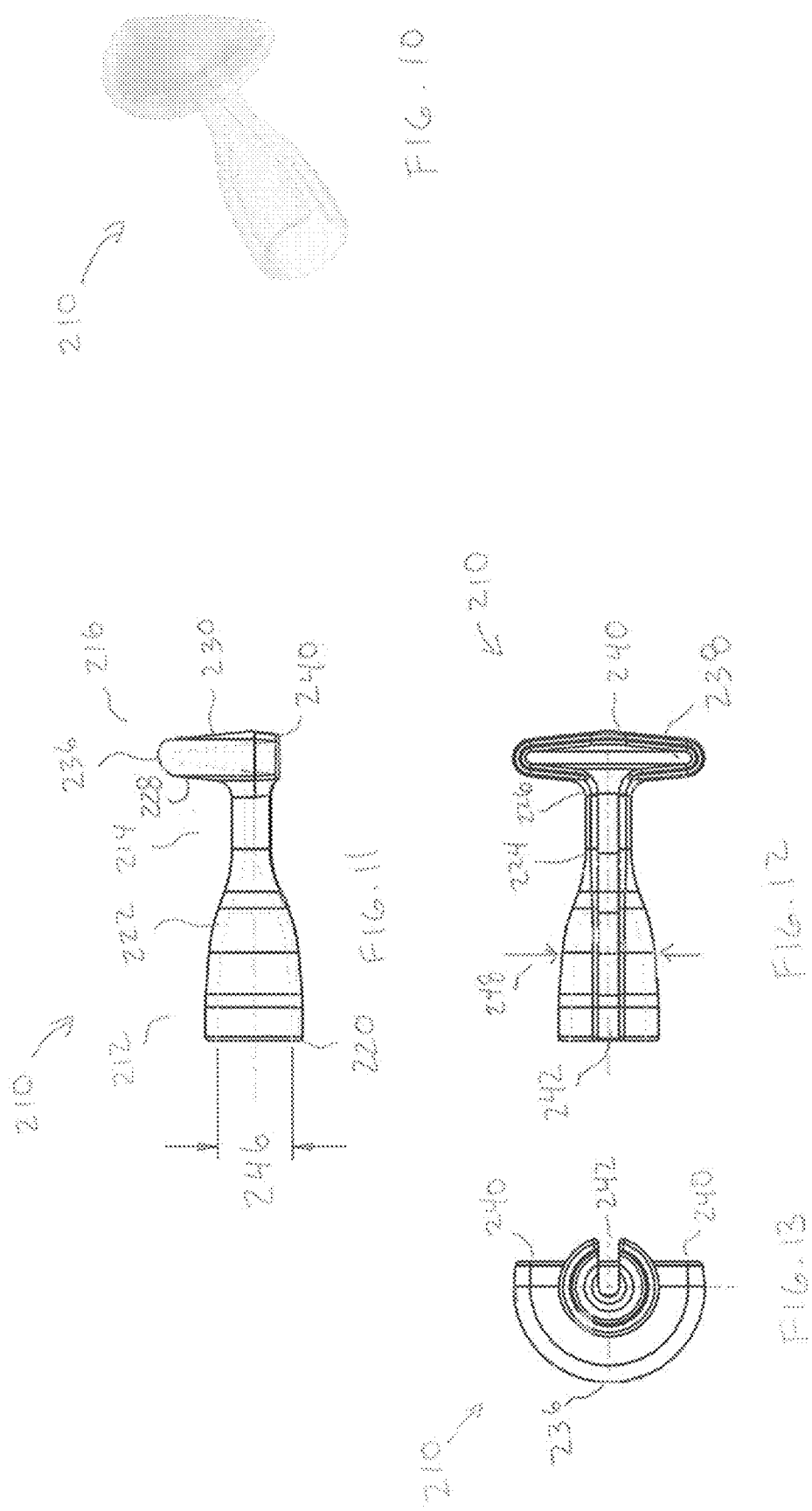

# REMOVABLE DENTAL MANDREL GUARD

CROSS-REFERENCE TO RELATED APPLICATIONS

This application is a nonprovisional of and claims priority to U.S. Provisional Application Ser. No. 61/860,441, filed Jul. 31, 2013, and which is herein incorporated by reference in its entirety.

FIELD OF THE INVENTION

The present invention relates to removable shields for dental instruments.

BACKGROUND

Power-driven dental mandrels have long been used in dentistry. Abrasive disks attachable to such mandrels for use in restorative work, to provide proximal contact adjustment and complete marginal seating of crowns, veneers, inlays/onlays, and proximal contouring of composite fillings is also known. However, current systems do not provide adequate safety to prevent inadvertent contact by the rotating disc (rotating at thousands of rpm) against the patient's mouth, which could cause severe injury. Additionally, current systems lack a safety mechanism to control absolute depth, or to prevent contact by the rotating shaft against a patient's adjacent teeth during use.

Providing a snap-on shield which surrounds the non-use (but still dangerous) side of the abrasive disk, and which extends to prevent contact by the rotating shaft against adjacent teeth, would provide substantially improved safety and permit the dentist to apply greater focus to the restoration work itself. Such a shield would also reduce possibility that material thrown from the abrasive disc will deposit on the dentist's safety glasses (thereby reducing visibility and safety) as well as reducing the amount of unwanted debris in the patient's mouth.

SUMMARY AND ADVANTAGES

A removable dental mandrel guard includes a collar portion, the collar having a hollow cylindrical interior cross-section with first interior diameter not greater than the diameter of the dental tool to which it is intended to attach, the collar portion extending from a first open end to a transition region along a longitudinal axis parallel with the mandrel shaft axis, the transition region reducing from the first interior diameter to a second interior diameter; a shaft guard extending from a first end rigidly connected to the transition region to a second end rigidly connected to the disc shield along a longitudinal axis parallel with the mandrel shaft axis, the shaft guard having a hollow cylindrical interior cross section defining the second interior diameter; a disc shield comprising opposed first and second transverse walls, each of the first and second transverse walls having a partially enclosed perimeter edge joined by coextensive edge wall extending from a first edge point to a second edge point, the interiors of the first and second transverse walls and edge wall defining a disc cavity; and, a continuous open seam extending longitudinally from the collar portion first open end to the shaft guard second end, the seam merging with the disc cavity.

A removable dental mandrel guard may include wherein the transition region reducing has a tapered hollow frustum profile. A removable dental mandrel guard may include wherein the transition region reducing comprises a tapered convex curve profile. A removable dental mandrel guard may include wherein the partial circumference defined by the first and second edge points extends at least 180°. A removable dental mandrel guard may include wherein the removable dental mandrel guard is made from polycarbonate. A removable dental mandrel guard may include wherein at least the disc shield is made from clear polycarbonate material. A removable dental mandrel guard may include wherein, the interior diameter of the collar portion first open end is not greater than 9 mm (0.35 inches).

The removable dental mandrel guard of the present invention presents numerous advantages, including: (1) improved safety against inadvertent contact with the interior parts of a patient's mouth and adjacent teeth; (2) improved safety through maximum depth control; (3) reduces the amount of debris in patients' mouths; (3) transparent for visibility; (4) quickly and easily mounted to a mandrel; (5) autoclavable; and, (6) disposable.

Additional advantages of the invention will be set forth in part in the description which follows, and in part will be obvious from the description, or may be learned by practice of the invention. The advantages of the invention may be realized and attained by means of the instrumentalities and combinations particularly pointed out in the appended claims. Further benefits and advantages of the embodiments of the invention will become apparent from consideration of the following detailed description given with reference to the accompanying drawings, which specify and show preferred embodiments of the present invention.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

FIG. 10 shows a perspective view of a third embodiment.
FIG. 11 shows a side view of a third embodiment.
FIG. 12 shows a bottom view of a third embodiment.
FIG. 13 shows an end view of a third embodiment.

REFERENCE NUMBERS USED IN DRAWINGS

Figure 1:
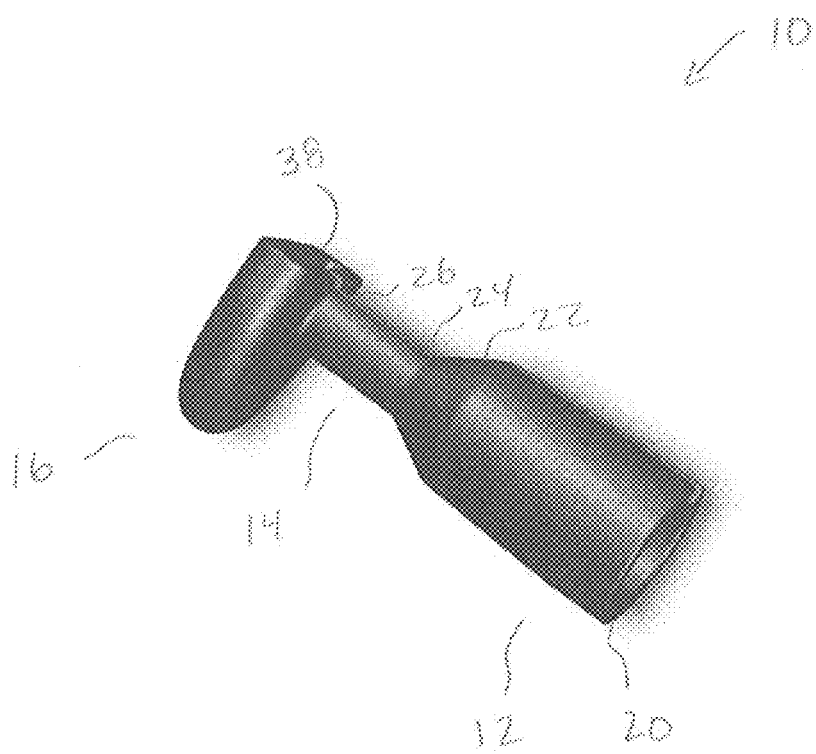
FIG. 1 shows side view of a first embodiment.

Turning now descriptively to the drawings, in which similar reference characters denote similar elements throughout the several views, the figures illustrate the _of the present invention. With regard to the reference numerals used, the following numbering is used throughout the various drawing figures:
10 First embodiment
12 Collar portion 14 Shaft guard portion
16 Disc guard portion
18 Disc
20 Collar portion first open end
22 Collar portion transition region
24 Shaft guard portion first end
26 Shaft guard portion second end
28 Disc guard portion first transverse wall
30 Disc guard portion second transverse wall
32 First transverse wall perimeter edge
34 Second transverse wall perimeter edge
36 Edge wall
38 Disc cavity
40 Disc guard portion open edge
42 Open seam
44 Abrasive disc perforations
46 Collar portion first diameter
48 Collar portion second diameter
110 Second embodiment
112 Collar portion
114 Shaft guard portion
116 Disc guard portion
120 Collar portion first open end
122 Collar portion transition region
210 Third embodiment
212 Collar portion
214 Shaft guard portion
216 Disc guard portion
218 Disc
220 Collar portion first open end
222 Collar portion transition region
224 Shaft guard portion first end
226 Shaft guard portion second end
228 Disc guard portion first transverse wall
230 Disc guard portion second transverse wall
236 Edge wall
238 Disc cavity
240 Disc guard portion open edge
242 Open seam
246 Collar portion first diameter
248 Collar portion second diameter
D Dental driver
M Mandrel
P Polishing tool

DETAILED DESCRIPTION

Before beginning a detailed description of the subject invention, mention of the following is in order. When appropriate, like reference materials and characters are used to designate identical, corresponding, or similar components in differing figure drawings. The figure drawings associated with this disclosure typically are not drawn with dimensional accuracy to scale, i.e., such drawings have been drafted with a focus on clarity of viewing and understanding rather than dimensional accuracy.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Figure 2:
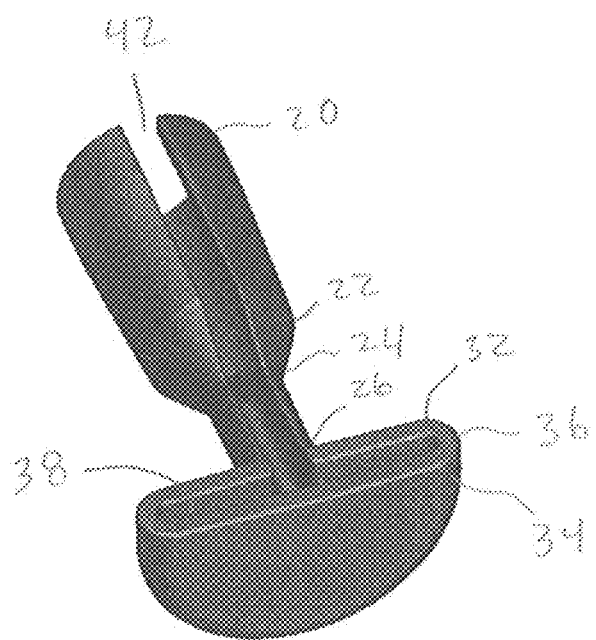
FIG. 2 shows a perspective view of a first embodiment.
Figure 3:
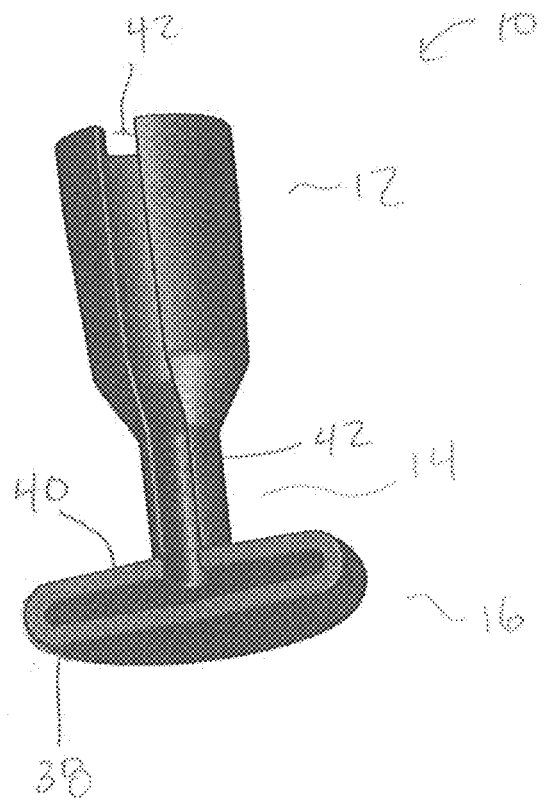
FIG. 3 shows another side view of a first embodiment.
Figure 4:
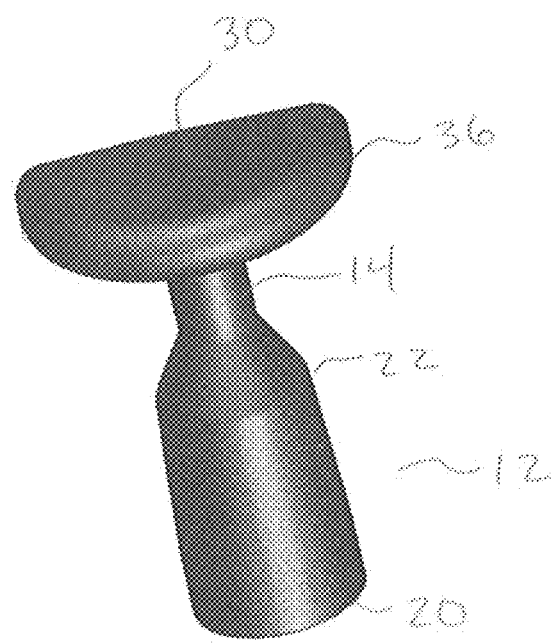
FIG. 4 shows another side view of a first embodiment.
Figure 5:
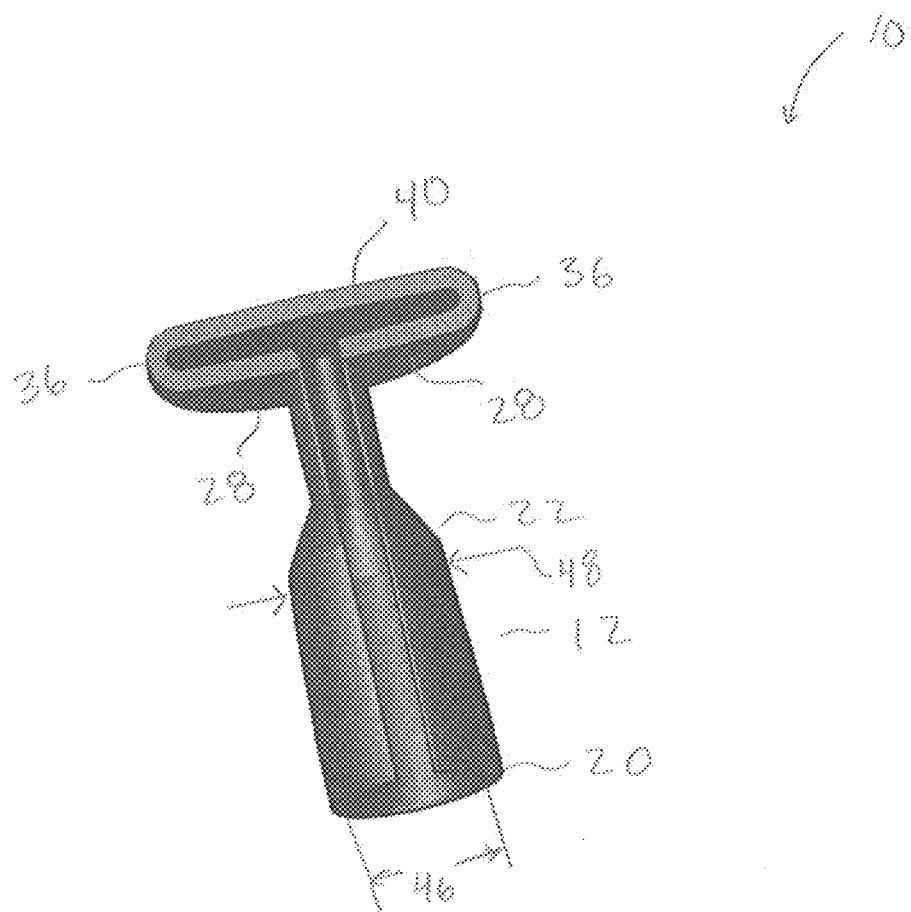
FIG. 5 shows another side view of a first embodiment.

As shown in FIGS. 1-5, a first embodiment of a removable dental mandrel guard 10 is provided, having a collar portion 12, a shaft guard portion 14 extending from collar portion 12, and disc shield portion 16 coupled to shaft guard portion 14 and adapted to partially enclose disc 18. Collar portion 12 includes a cylindrical cross section shaped to conform to the exterior of a selected dental mandrel shaft/handle, and extends from a first open end 20 to a transition region 22 where the collar portion 12 connects to shaft guard portion 14. In the described embodiment, collar portion 12 forms around cylindrical cross section. Collar first end 20 forms an opening having a first diameter 46 to receive the selected dental mandrel shaft/handle.

Shaft guard portion 14 forms cylindrical cross section extending from collar portion 12 at transition region 22. In the embodiment, shaft guard portion 14 is substantially narrower than collar portion 12, such that it closely encloses mandrel rotating shaft S without contacting the shaft. Transition region 22 includes a variable cross section which transitions from the larger cross section of collar portion 12 to the narrower cross section of shaft guard portion 14, but without creating sharp edges which would be uncomfortable contacting a patient's mouth or gums. In the embodiment, transition portion 22 cross section forms a frustum, providing greater strength to the unsupported shaft guard portion 14 and disc guard portion 16. Alternatively, transition portion 22 could comprise a shoulder profile. Shaft guard portion 16 extends from a first end 24, proximate and connected to transition region 22, to a second end 26 which provides connection to disc guard portion 16.

Collar portion 12 has a hollow cylindrical interior cross-section with first interior diameter 46 not greater than the diameter of the mandrel M to which it is intended to attach, and being slightly tapered to second interior diameter 48 proximate transition region 22, to ensure positive grip. Transition region 22 tapers more steeply from the second interior diameter 46 to a third interior diameter corresponding to shaft guard portion 14. In the embodiment, first interior diameter 46 is 9 mm (0.35 inches), to fit snuggly to standard sized dental mandrel, and third interior diameter is 2.5 mm (0.1 inches) to provide adequate clearance for a mandrel shaft.

Disc guard portion 16 is connected to shaft guard portion 14 at its second end 26. Disc guard portion 16 includes opposed first and second transverse walls 28 and 30, respectively, each having a partial circular perimeter edge 32 and 34, respectively. Edge wall 36 spans from first to second perimeter edges 32, 34, respectively, to form disc cavity 38. In practice, first and second transverse walls 28, 30, and edge wall 36 may be formed together to create a seamless transition rather than discrete parts, as in the described embodiment. Perimeter edges 32, 34 and enclosing edge wall 36, extend circumferentially to form a partial circle or oval, providing an uncovered region through which a portion of disc 18 is exposed for insertion between teeth, defined by disc guard portion open edge 40. In the described embodiment, perimeter edges 32, 34 and edge wall 36 extend greater than 180° as the walls extend beyond the circular center point, but they may extend more or less depending on the needs of the user. In the embodiment, perimeter edges 32, 34 and edge wall 36 extend straight and parallel beyond the mandrel centerline axis to form a partial straight-sided oval or racetrack profile. Disc guard portion open edge 40 may extend farther, thereby limiting the depth to which disc 18 may be inserted into the interstitial space between the teeth for added safety.

In the embodiment, collar portion 12 and shaft guard portion 14 include a continuous open seam 42 extending longitudinally from to disc guard portion 16, which permits easy insertion onto dental mandrel M, and removal after use.

Figure 6:
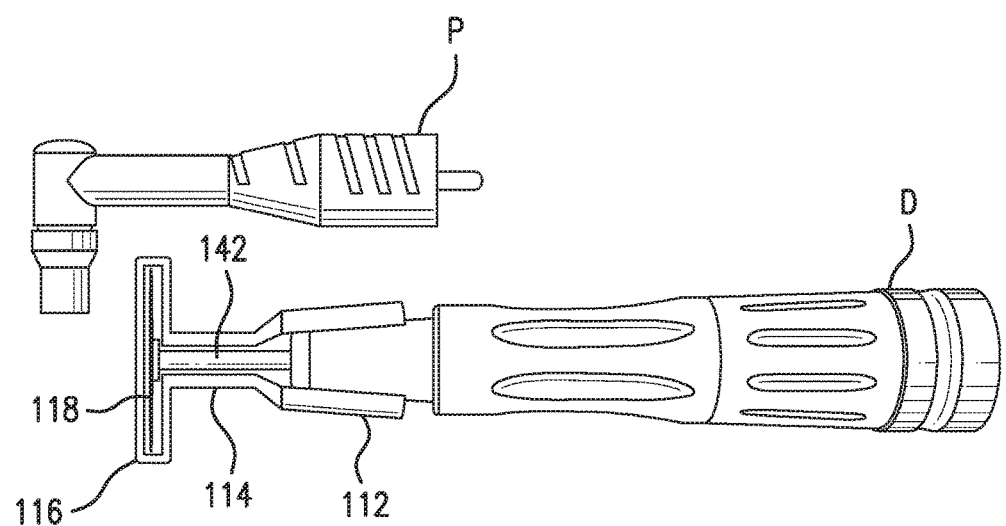
FIG. 6 shows a second embodiment mounted onto a dental mandrel tool, with exemplary dimensions.
Figure 7:
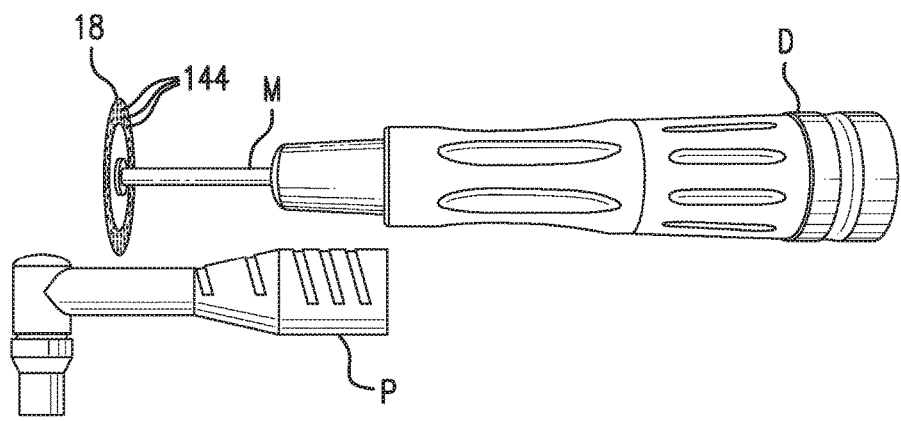
FIG. 7 shows a side view of a second embodiment mounted to a dental driver D, with a dismounted polishing tool P shown for orientation and proportion, and including a perforated disc.
Figure 8:
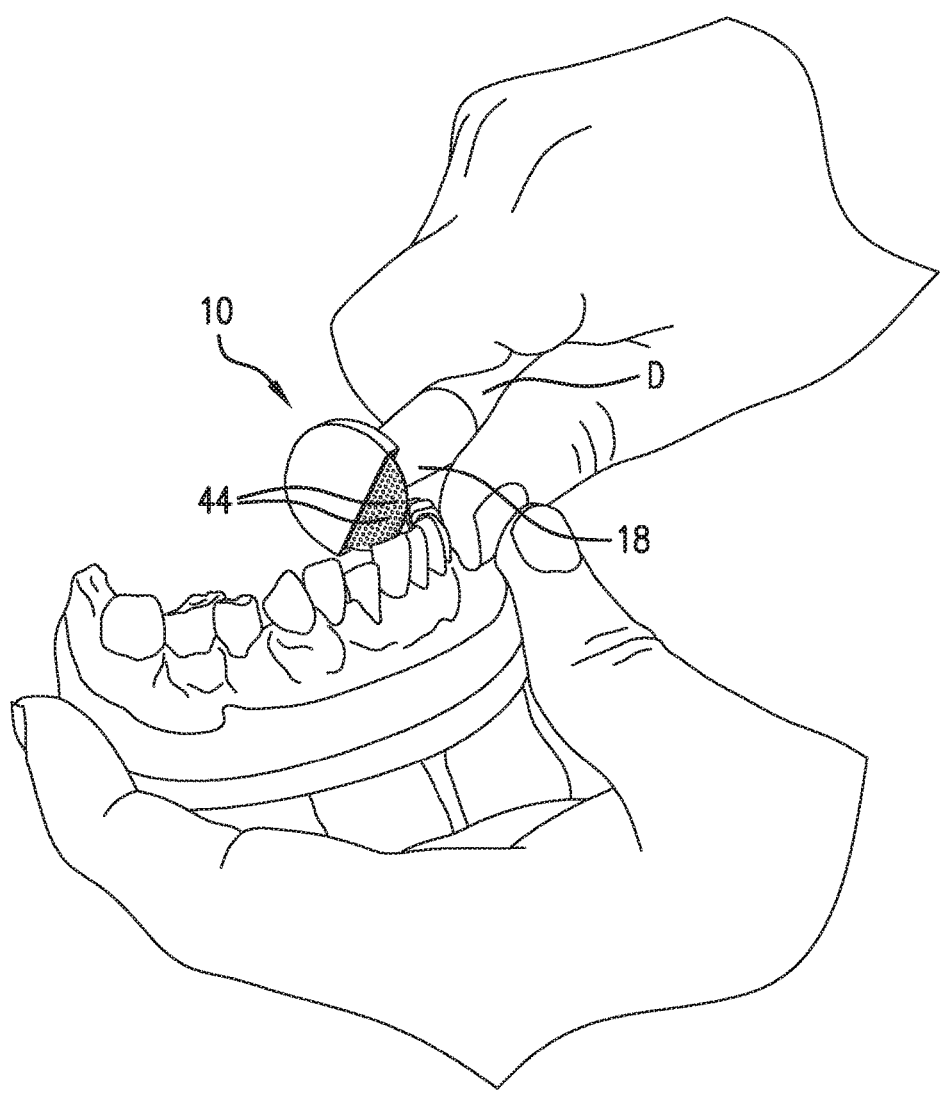
FIG. 8 shows a demonstration of use of a second embodiment, with a perforated disc.
Figure 9:
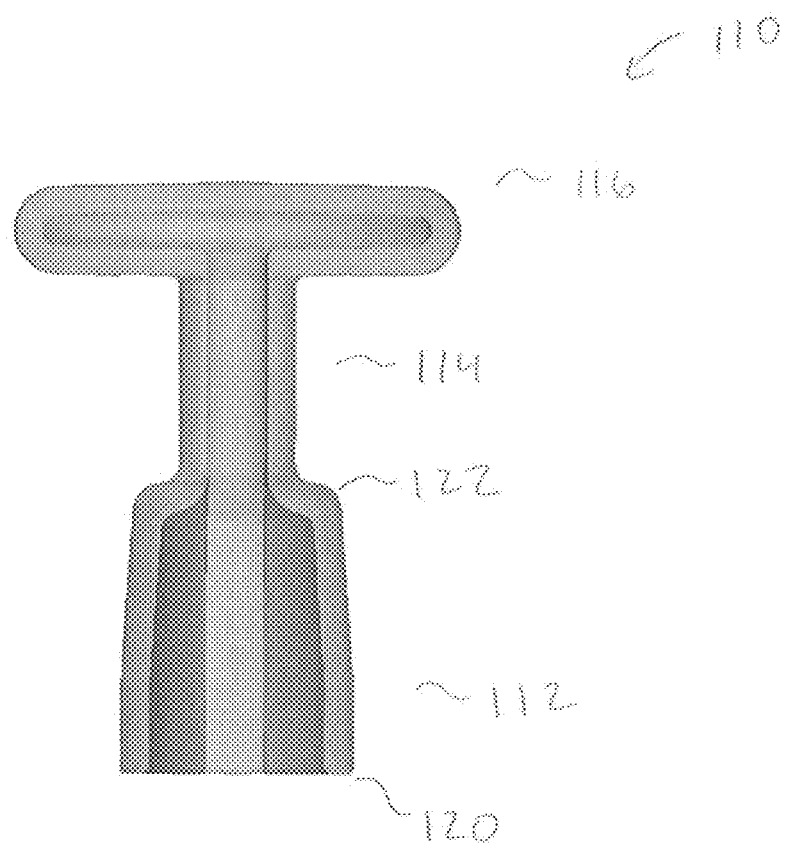
FIG. 9 shows a bottom view of a second embodiment.

Referring to FIGS. 6-9, a second embodiment 110 is shown, generally similar to the first embodiment, but including a shoulder transition region 122, having a collar portion 112, a shaft guard portion 114 extending from collar portion 112, and disc shield portion 116 coupled to shaft guard portion 114 and adapted to partially enclose a disc 18. Collar portion 112 includes a cylindrical cross section shaped to conform to the exterior of a selected dental mandrel shaft/handle, and extends from a first open end 120 to a transition region 122 where the collar portion 112 connects to shaft guard portion 114.

Referring to FIGS. 10-13, a third embodiment 210 is shown generally similar to the first embodiment 10, having a collar portion 212, a shaft guard portion 214 extending from collar portion 212, and disc shield portion 216 coupled to shaft guard portion 214 and adapted to partially enclose disc 18. Collar portion 212 includes a cylindrical cross section shaped to conform to the exterior of a selected dental mandrel shaft/handle, and extends from a first open end 220 to a transition region 222 where the collar portion 212 connects to shaft guard portion 214. In the described embodiment, collar portion 212 forms a round cylindrical cross section. Collar first end 220 forms an opening having a first diameter 246 to receive the selected dental mandrel shaft/handle.

Shaft guard portion 214 forms cylindrical cross section extending from collar portion 212 at transition region 222. In the embodiment, shaft guard portion 214 is substantially narrower than collar portion 212, such that it closely encloses mandrel rotating shaft S without contacting the shaft. Transition region 222 includes a variable cross section which tapers from the larger cross section of collar portion 212 at second diameter 248 to the narrower cross section of shaft guard portion 214, but without creating sharp edges which would be uncomfortable contacting a patient's mouth or gums or create stress concentration regions. In the embodiment, transition portion 222 cross section forms a curved taper, providing greater strength to the unsupported shaft guard portion 214 and disc guard portion 216. Shaft guard portion 216 extends from a first end 224, proximate and connected to transition region 222, to a second end 226 which provides connection to disc guard portion 216.

Collar portion 212 has a hollow cylindrical interior cross-section with first interior diameter 246 not greater than the diameter of the mandrel M to which it is intended to attach, and being slightly tapered to second interior diameter 248 proximate transition region 222, to ensure positive grip. Transition region 222 tapers more steeply from the second interior diameter 248 to a third interior diameter corresponding to shaft guard portion 214.

Disc guard portion 216 is connected to shaft guard portion 214 at its second end 226. Disc guard portion 216 includes opposed first and second transverse walls 228 and 230, respectively, each having a partial circular perimeter edge. Edge wall 236 spans from first to second perimeter edges, to form disc cavity 238. In practice, first and second transverse walls 228, 230, and edge wall 236 may be formed together to create a seamless transition rather than discrete parts, as in the described embodiment. The perimeter edges and enclosing edge wall 236, extend circumferentially to form a partial circle or oval, providing an uncovered region through which a portion of disc 18 is exposed for insertion between teeth, defined by disc guard portion open edge 240. In the described embodiment, the perimeter edges and edge wall 236 extend greater than 180° as the walls extend beyond the circular center point, but they may extend more or less depending on the needs of the user. Disc guard portion open edge 240 may extend farther, thereby limiting the depth to which disc 18 may be inserted into the interstitial space between the teeth for added safety.

In the embodiment, collar portion 212 and shaft guard portion 214 include a continuous open seam 242 extending longitudinally from to disc guard portion 216, which permits easy insertion onto dental mandrel M, and removal after use.

In practice, a dental mandrel guard 10 may be manufactured using injection molding methods to form a unitary piece, rather than separation pieces connected together. In the embodiment, dental mandrel guard 10 is formed from clear polycarbonate, which can be sterilized in an autoclave or similar process, provides adequate balance between hardness and rigidity, to provide safety, and flexibility to allow the guard to go over a mandrel and provide an adequate compression grip. The exterior surface is smooth to provide for effective sterilization, but not glossy.

An improved abrasive mandrel disc 18 is provided, having a plurality of perforations 44 disposed evenly about the disc 18. In use, enamel material removed from the target region is trapped within the perforations 44 to be carried out when that portion of disc 18 passes out of the interstitial region, ejecting the removed material.

Those skilled in the art will recognize that numerous modifications and changes may be made to the preferred embodiment without departing from the scope of the claimed invention. It will, of course, be understood that modifications of the invention, in its various aspects, will be apparent to those skilled in the art, some being apparent only after study, others being matters of routine mechanical, chemical and electronic design. No single feature, function or property of the preferred embodiment is essential. Other embodiments are possible, their specific designs depending upon the particular application.

We claim:

1. A removable dental mandrel guard, the mandrel shaft defining a longitudinal axis, the guard comprising:
    a collar portion extending from a first open end to a transition region along a longitudinal axis parallel mandrel shaft axis, the collar including a first portion comprising a hollow cylindrical interior cross-section with first interior diameter not greater than the diameter of the dental tool to which it is intended to attach and a second interior diameter proximate the transition region, the transition region reducing from the second interior to a third interior diameter;
    a shaft guard extending from a first end rigidly connected to the transition region to a second end rigidly connected to the disc shield along a longitudinal axis parallel with the mandrel shaft axis, the shaft guard having a hollow cylindrical interior cross section extending greater than 180 degrees in circumference defining the third interior diameter;
    a disc shield comprising opposed first and second transverse walls, each of the first and second transverse walls having a partially enclosed perimeter edge joined by coextensive edge wall extending from a first edge point to a second edge point, the second transverse wall extending transversely from the first edge point to the second edge point, the interiors of the first and second transverse walls and edge wall defining a disc cavity; and, a continuous open seam extending longitudinally from the collar portion first open end to the shaft guard second end, the seam merging with the disc cavity.

2. The apparatus of claim 1, further comprising:
wherein the collar second diameter is equal to the first diameter.

3. The apparatus of claim 1, further comprising:
wherein the collar first portion is tapered from the first diameter to the second diameter, defining a first tapered portion, and the transition region reduction is greater than the reduction of the first tapered portion.

4. The apparatus as in claim 1, further comprising:
wherein the transition region reducing comprises a tapered hollow frustum profile.

5. The apparatus as in claim 1, further comprising:
wherein the transition region reducing comprises a tapered convex curve profile.

6. The apparatus as in claim 1, further comprising:
wherein the transition region reducing comprises a tapered convex-to-concave curve profile.

7. The apparatus as in claim 1, further comprising
wherein the partial circumference defined by the first and second edge points extends at least 180.

8. The apparatus as in claim 1, further comprising:
wherein the removable dental mandrel guard is made from polycarbonate.

9. The apparatus as in claim 1, further comprising:
wherein at least the disc shield is made from clear polycarbonate material.

10. The apparatus as in claim 1, further comprising:
wherein, the interior diameter of the collar portion first open end is not greater than 9 mm (0.35 inches).

11. The apparatus as in claim 1, further comprising:
wherein the first and second perimeter edges and edge wall extend beyond the mandrel shaft axis.

* * * * *